US00PP27007P3

(12) United States Plant Patent
Skotak, Jr.

(10) Patent No.: US PP27,007 P3
(45) Date of Patent: Aug. 2, 2016

(54) ***GUZMANIA* PLANT NAMED 'DURAJUL'**

(50) Latin Name: ***Guzmania* hybrid**
Varietal Denomination: DURAJUL

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 88 days.

(21) Appl. No.: 14/121,586

(22) Filed: Sep. 19, 2014

(65) Prior Publication Data

US 2016/0088784 P1 Mar. 24, 2016

(51) Int. Cl.
*A01H 5/02* (2006.01)

(52) U.S. Cl.
USPC ..... Plt./371

(58) Field of Classification Search
USPC ..... Plt./371
See application file for complete search history.

*Primary Examiner* — Annette Para
(74) *Attorney, Agent, or Firm* — Cassandra Bright

(57) ABSTRACT

A new and distinct *Guzmania* cultivar named 'DURAJUL' is disclosed, characterized by very wide flower of unusual pink and purple coloration. The new variety is an *Guzmania*, typically produced as an indoor ornamental plant.

1 Drawing Sheet

Latin name of the genus and species: *Guzmania* hybrid.
Variety denomination: 'DURAJUL'.

BACKGROUND OF THE INVENTION

The new cultivar is a product of a planned breeding program. The objective of the planned breeding program was to develop new *Guzmania* varieties for commercial ornamental purposes. The new variety originated from a cross pollination of an unnamed, unpatented proprietary *Guzmania* hybrid seed parent with an unnamed, unpatented, *Guzmania lingulata* as the pollen parent. The crossing was made during 2007 in a commercial greenhouse in Alajuela, Costa Rica.

The new variety was discovered by the inventor, Chester Skotak jr., a citizen of Costa Rica, in January of 2009 in a group of seedlings resulting from the crossing. The new cultivar was found in a commercial greenhouse in Alajuela, Costa Rica.

Asexual reproduction of the new cultivar 'DURAJUL' was first performed at a commercial laboratory in Belgium by tissue culture during September, 2010. Subsequent propagation by tissue culture has shown that the unique features of this cultivar are stable and reproduced true to type.

SUMMARY OF THE INVENTION

The cultivar 'DURAJUL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DURAJUL.' These characteristics in combination distinguish 'DURAJUL' as a new and distinct *Guzmania* cultivar:

1. Unusual pink and purple flower coloration.
2. Very wide inflorescence.
3. Greyed-Purple anthocyanin coloration of foliage.

PARENT COMPARISON

Plants of the new cultivar 'DURAJUL' are similar to seed parent in most horticultural characteristics. The new variety however differs in the following characteristics:

1. More compact plant.

Plants of the new cultivar 'DURAJUL' are similar to the pollen parent, in most horticultural characteristics. The new variety however differs in the following characteristics:

1. Larger plant size.

COMMERCIAL COMPARISON

'DURAJUL' can be compared to the commercial variety of *Guzmania* know as 'Freya', U.S. Plant Pat. No. 21,461. Plants of *Guzmania* 'Freya' are similar to plants of 'DURAJUL' in most horticultural characteristics. However 'DURAJUL' differs from *Guzmania* in the following characteristics:

1. Pink and purple flowers. The comparator has purple flowers
2. Much more anthocyanin coloration of the underside of the leaves.

'DURAJUL' can be compared to the commercial variety of *Guzmania* know as 'Viola', U.S. Plant Pat. No. 13,679. Plants of *Guzmania* 'Viola' are similar to plants of 'DURAJUL' in most horticultural characteristics. However 'DURAJUL' differs from *Guzmania* in the following characteristics:

1. Darker flower color.
2. Darker green leaves.
3. Larger plant size.

BRIEF DESCRIPTION OF THE PHOTOGRAPH

The accompanying photograph in FIG. 1 illustrates in full color a typical plant of 'DURAJUL' grown in a greenhouse in Belgium. This plant is approximately 20 months old, shown in an 12 cm. pot.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'DURAJUL' plants grown in a climate controlled greenhouse in Evergem, Belgium. Temperatures ranged from 18° C. to 22° C. at night to 20° C. to 28° C. during the day. No artificial light, photoperiodic or chemical treatments were given to the plants. Measurements and numerical values represent averages of typical plant types.

Botanical classification: *Guzmania* hybrid 'DURAJUL'.

PROPAGATION

First propagation method: Tissue culture.

Type of propagation typically used: Tissue culture.

Time to initiate roots: About 15 days at approximately 20° C.

Time to produce a rooted cutting/liner: About 180 days at approximately 22° C.

Root description: Moderately dense, moderately branched, fine, fibrous, not fleshy, colored near RHS Brown 200A, 200B, 200C and 200D.

PLANT

Growth habit: Upright, monopodial.

Height: Average: 41.0 cm.

Plant spread: Average: 52.2 cm.

Normal pot size: 12 cm (circular).

Growth rate: Moderate.

Branching characteristics: Monopodial, leaves form a basal rosette, inflorescence grows from the center of the rosette.

Number of leaves per scape: Average: 15.

Stem length: No stems present, scape grows directly from rosette.

FOLIAGE

Leaf:

*Arrangement*.—Rosulate; leaves (average: 15) placed in a basal rosette.

*Average length*.—Approximately 33.0 cm.

*Average width*.—Approximately 4.2 cm (measured at 50% of the leaf blade).

*Shape of blade*.—Ligulate.

*Aspect*.—Base in an average angle of 45° to horizontal, tip arching to horizontal (=0°), outer tip curved downward in an average angle of −90° to horizontal.

*Apex*.—Apiculate, outer tip curved downward in an average angle of −90° to horizontal.

*Base*.—Sheathing. Sheath length: Average 8.0 cm. Sheath width: Average 7.4 cm. Sheath color: Yellow-green, near RHS 152B, striped greyed-purple; near RHS 183A to 183B.

*Margin*.—Entire.

*Texture of top surface*.—Glabrous, glossy.

*Texture of bottom surface*.—Glabrous, glossy.

*Color*.—Young foliage upper side: Yellow-green; near RHS 147A. Young foliage under side: Yellow-green; near RHS 148A but darker, striped and tinged greyed-purple; near RHS 183A to 183B. Mature foliage upper side: Yellow-green; near RHS 147A. Mature foliage under side: Yellow-green; near RHS 148A but darker, heavily striped and tinged greyed-purple; near RHS N186C and 187A.

*Venation*.—Type: Parallel. Venation coloration: As leaf blade; upper side yellow-green; near RHS 147A, under side yellow-green; near RHS 148A but darker, heavily striped and tinged greyed-purple; near RHS N186C and 187A.

Petiole: No petioles present, leaves sheathing.

INFLORESCENCE

General description:

*Inflorescence height, excluding scape*.—Approximately 12.6 cm.

*Inflorescence width*.—Approximately 20.1 cm.

Scape:

*Length*.—Approximately 28.4 cm.

*Width*.—Approximately 1.0 cm.

*Aspect*.—Approximately 90° angle to rosette (near vertical).

*Strength*.—Very strong.

*Color*.—Yellow-green, near RHS 145C.

Bracts:

*Scape/lowermost bracts*.—Shape: Ligulate. Length: Approximately 21.7 m (excluding sheath). Width: Approximately 4.4 cm (measured at 50% of the leaf blade). Quantity: Average 8. Tip: Apiculate, outer tip curved downward in an average angle of −90° to horizontal. Base: Sheathing. Sheath length: Approximately 5.2 cm. Sheath width: Approximately 5.7 cm. Sheath color: Yellow-green to greyed-yellow; in between near RHS 151A and 160A, striped greyed-purple; near RHS 183C and 187A. Margin: Entire. Color upper side: Greyed-red; near RHS 181A, top green to yellow-green; in between near RHS N137A and 147A but much darker. Color under side: Greyed-red; near RHS 181A, top brown; near RHS 200B.

Terminal bracts:

*Shape*.—Ligulate.

*Length*.—Approximately 10.9 cm (incl. sheath).

*Width*.—Approximately 3.4 cm (measured at 50% of the leaf blade).

*Quantity*.—Average 16.

*Tip*.—Apiculate to long acute, outer tip curved to horizontal (=0°).

*Base*.—Sheathing. Sheath length: Approximately 5.0 cm. Sheath width: Approximately 6.0 cm. Sheath color: Greyed-yellow; near RHS 160D.

*Margin*.—Entire.

*Coloration terminal bracts*.—Upper side: Red-purple; near RHS 60A, colored more red towards the top; near RHS 53C, outer tip brown; near RHS 200B to 200C. Under side: Red-purple; near RHS 60B, colored more red towards the top; near RHS 53C, outer tip brown; near RHS 200B to 200C.

OTHER CHARACTERISTICS

Disease resistance: Neither resistance nor susceptibility to the normal diseases and pests of *Guzmania* has been observed.

Drought tolerance and cold tolerance: Observed to tolerate temperatures to 40° C. without any negative effects. Temperature tolerance above this range has not been observed. Tolerance of cold temperatures has not been observed.

Fruit/seed production: No production observed to date.

What is claimed is:

1. A new and distinct cultivar of *Guzmania* plant named 'DURAJUL' as herein illustrated and described.

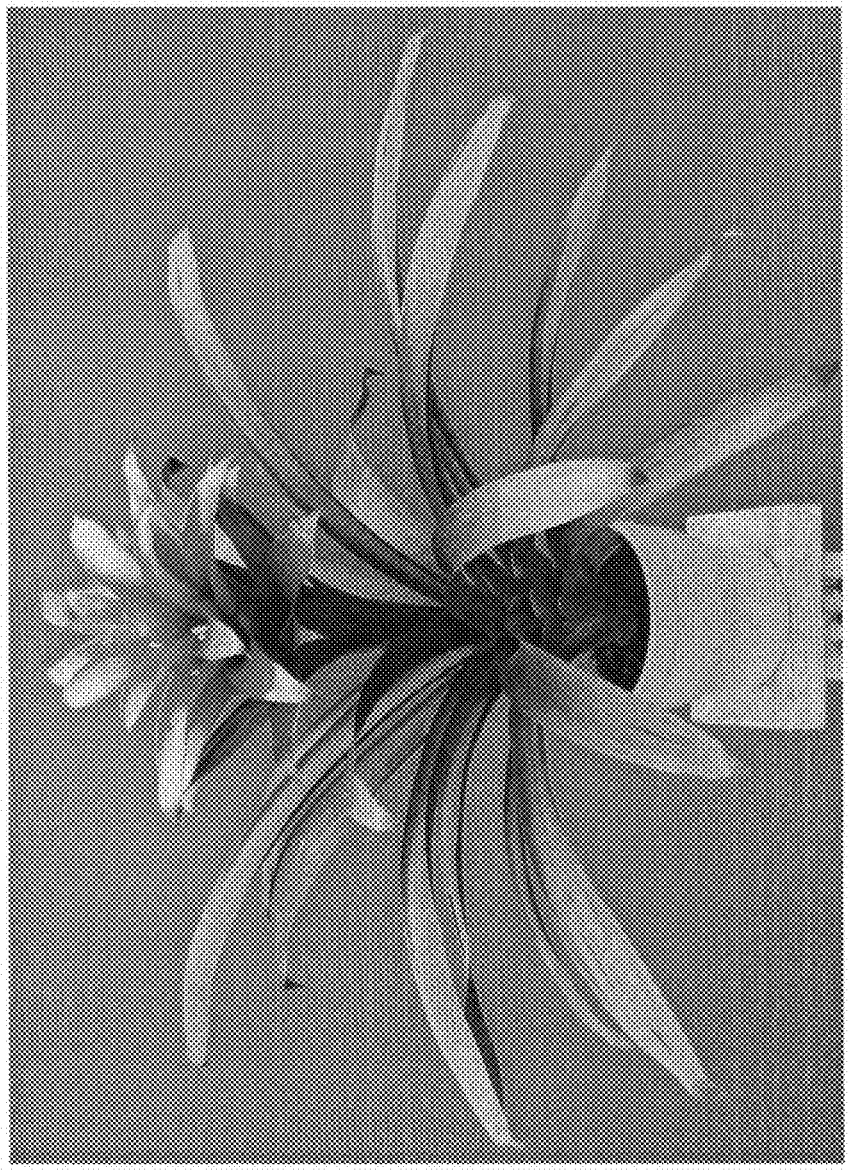

* * * * *